(12) United States Patent
Reinstein et al.

(10) Patent No.: US 8,444,632 B2
(45) Date of Patent: May 21, 2013

(54) METHOD OF PERFORMING REFRACTIVE LASER EYE SURGERY CENTERED ALONG THE VISUAL AXIS OF A HUMAN EYE

(75) Inventors: Dan Z. Reinstein, London (GB); Hartmut Vogelsang, Jena (DE); Daniel Neal, Tijeras, NM (US)

(73) Assignee: Carl Zeiss Meditec AG, Jena (DE)

( * ) Notice: Subject to any disclaimer, the term of this patent is extended or adjusted under 35 U.S.C. 154(b) by 657 days.

(21) Appl. No.: 12/612,898

(22) Filed: Nov. 5, 2009

(65) Prior Publication Data

US 2010/0114076 A1    May 6, 2010

Related U.S. Application Data

(60) Provisional application No. 61/198,494, filed on Nov. 5, 2008.

(51) Int. Cl.
*A61B 18/18*    (2006.01)
*A61B 3/10*    (2006.01)

(52) U.S. Cl.
USPC ................ 606/4; 351/205; 351/212; 351/246

(58) Field of Classification Search
USPC ............... 606/4, 5, 10–12; 128/898; 351/204, 351/205, 211, 212, 246, 247
See application file for complete search history.

(56) References Cited

U.S. PATENT DOCUMENTS 6,572,607 B2 * 6/2003 Clapham ........................... 606/5
2009/0033867 A1 * 2/2009 Dai ............................... 351/205

OTHER PUBLICATIONS

American National Standards for Opthalmics: Methods for Reporting Optical Aberrations of the Eyes. ANSI Z80.28-2004, 2004.

* cited by examiner

*Primary Examiner* — Huy K Mai
(74) *Attorney, Agent, or Firm* — Leydig, Voit & Mayer, Ltd.

(57) ABSTRACT

A method of performing refractive laser eye surgery on a human eye is provided wherein the ablation pattern is centered along the visual axis, rather than along the line of sight. First, a wavefront, either ocular, corneal or a combination thereof, is generated by a wavefront sensor centered along the line of sight. This measured wavefront is centered on and encompasses a patient's pupil. Then, an analysis pupil is determined which encompasses the measured pupil. The analysis pupil is centered along the visual axis at the point of intersection with the cornea. Consequently, the measured wavefront is reconstructed over the analysis pupil only using data taken over the area covered by the measured pupil. This reconstruction is done through a least squares fit of a series of slopes from the measured wavefront and/or through the transformation of aberration coefficients. Finally, an ablation pattern, or a lenticule generation pattern, to be performed by a refractive laser centered on the corneal intersect of the visual axis is produced in accordance with the reconstructed wavefront.

19 Claims, 3 Drawing Sheets

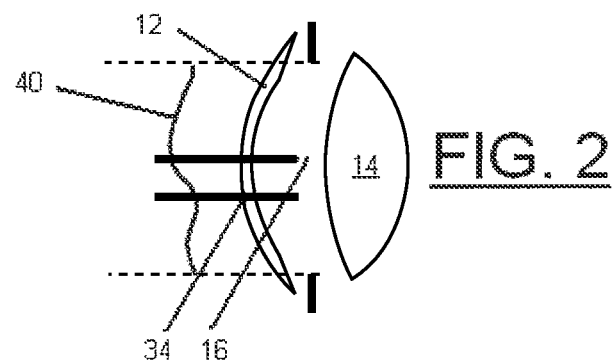
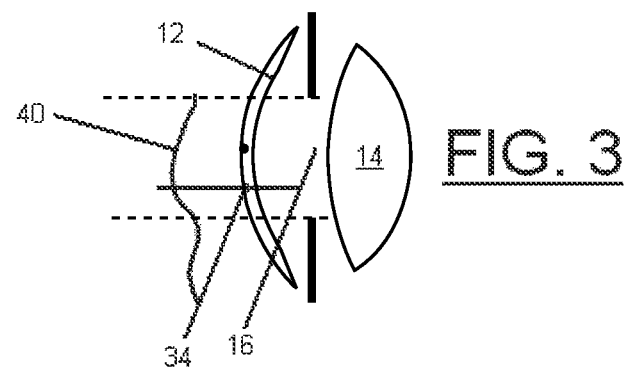
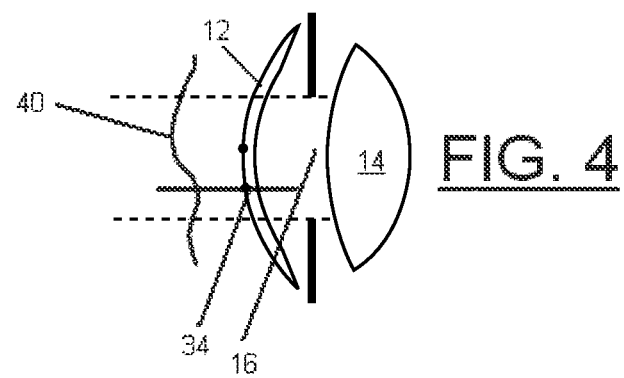

METHOD OF PERFORMING REFRACTIVE LASER EYE SURGERY CENTERED ALONG THE VISUAL AXIS OF A HUMAN EYE

CROSS REFERENCE TO PRIOR APPLICATIONS

Priority is claimed to U.S. Provisional Patent Application Ser. No. 61/198,494, filed on Nov. 5, 2008, the entire disclosure of which is hereby incorporated by reference herein.

FIELD

The present invention generally relates to refractive laser surgery for vision correction, and more specifically to a method of correcting spherocylindrical and higher order aberrations of the human eye.

BACKGROUND

Many people suffer from poor vision due to spherocylindrical aberrations of the human eye and require the use of corrective contact lenses or glasses. However, the refractive state of the eye may be improved by refractive laser eye surgery in order to decrease or eliminate this dependency on contact lenses or glasses. Refractive laser eye surgery is a procedure performed on patients by ophthalmologists to correct common vision disorders such as myopia, hyperopia and astigmatism. The most common method of refractive laser eye surgery uses an excimer laser to reshape the cornea. Some variations of this technique are Photorefractive Keratectomy (PRK), Laser Assisted In-Situ Keratomileusis (LASIK), Laser Assisted Sub-Epithelium Keratomileusis (LASEK), epi-LASIK, sub-Bowman's Keratomileusis and femtosecond corrective procedures, such as Femtosecond Lenticule Extraction (FLEx).

In most refractive laser surgery techniques, the cornea is reshaped by excimer laser ablation of corneal tissue either on the surface (e.g., as in PRK, LASEK and epi-LASIK) or within the stroma (e.g., as in LASIK and sub-Bowman's Keratomileusis) by creating a flap of corneal tissue which is subsequently flipped up or removed prior to ablation and later replaced. In FLEx, a femtosecond laser is used to create both a flap and a lenticule of intrastromal corneal tissue, the latter of which is removed to provide the optical correction. In addition, femtosecond disrupted tissue may be absorbed by surrounding tissue, thereby causing a change in the corneal structure/curvature and effecting the refractive state of the eye as well. One such femtosecond laser is marketed under the trade name VisuMax® by Carl Zeiss Meditec AG.

Customized ablation patterns for the lasers may be calculated from ocular wavefront data taken by a wavefront aberrometer, such as a Shack-Hartmann wavefront sensor. Alternatively, the ablation patterns may be determined from corneal topography or calculated from corneal wavefront data, which relies on corneal topography measurements. In each case, this process often results in the generation of Zernike polynomials which describe the aberrations of the cornea or of the complete eye from an ideal spherical shape. Each Zernike polynomial is weighted by a Zernike coefficient. The Zernike coefficients may be transformed using an available algorithm. One such method is described in American National Standards for Opthalmics: Methods for Reporting Optical Aberrations of the Eyes, ANSI Z80.28—2004, 2004, the entire disclosure of which is incorporated herein by reference.

The foregoing excimer ablation techniques typically center the ablation pattern of the excimer laser on the center of the pupil. Similarly, the corneal dissections which form the lenticules in femtosecond corrective procedures are also typically centered to the pupil. To provide this alignment, a patient focuses on a fixation target which is aligned with the optical axis of the laser. In excimer ablation procedures, an eye tracking system is provided to allow for continuous recalculation and adjustment to the center of the pupil in order to assure proper alignment of the laser throughout the procedure. In femtosecond corrective procedures, a rigid connection is provided between the optical femtosecond laser aperture and a contact glass which is provided at the cornea and centrally adapted to the pupil. This path, which is defined from the center of the pupil to the center of the fixation target when a patient focuses thereon, will hereinafter be referred to as the line of sight.

However, the line of sight does not represent a person's actual physiological visual sighting axis. The physiological sighting axis, which hereinafter will be referred to as the visual axis, for a human eye fixating on a target is defined from the real foveal image, where the light passes through the nodal points of the eye as determined by geometric construction principles, to the center of the fixation target. The visual axis and the line of sight will differ by varying degrees among individuals.

SUMMARY

From a physiological standpoint, more accurate results may be obtained by aligning the visual axis, rather than the line of sight, with the optical axis of the laser. In other words, in some cases or based on a surgeon's preferences, the ablation pattern should be centered on the intersection of the visual axis and the cornea, rather than the center of the pupil, to provide proper customized vision correction. This is especially true for individuals who have a greater degree of variance between their line of sight and visual axis. However, centration along the visual axis has heretofore not been possible correctly when the ablation pattern is based on ocular or corneal wavefront data.

The present invention provides a method for reconstructing ocular or corneal wavefront data in order to provide a shift and allow for customized ablation which is centered along the visual axis.

The ablation pattern taken by a refractive laser during refractive laser eye surgery is defined by a wavefront that is measured with respect to the center of the pupil along the line of sight. However, this wavefront may not always accurately represent aberrations from a patient's perspective since the patient focuses on a fixation target along the visual axis of the eye rather than along the line of sight. In accordance with the present invention, a method for shifting and reconstructing and/or reexpanding the measured wavefront is provided to define an ablation pattern that will be centered at the corneal intersect of the visual axis, rather than at the center of the pupil along the line of sight.

The measured wavefront is typically quantified in terms of polynomials, such as Zernike polynomials, each of which is weighted by Zernike coefficients. The Zernike coefficients are transformed to account for the shift to the corneal intersect of the visual axis and any change in diameter from the size of the originally measured pupil. These new Zernike coefficients can then be used to reconstruct the measured wavefront and determine an ablation pattern which is centered on the corneal intersect of the visual axis. Alternatively, primary data, such as wavefront slope data, and secondary raw data, such as reconstructed wavefront height data expanded through a set of Zernike aberrations, taken from an aberrometer, such as a Shack-Hartmann wavefront sensor, could be used in a single step to reconstruct a wavefront over the corneal intersect of the visual axis in a single step, e.g., by performing a least squares fit of slope data over the area covered by the shifted wavefront and within the original measurement area.

By reconstructing the wavefront over the corneal intersect of the visual axis, a combined customized ablation pattern covering both spherocylindrical corrections and higher order aberrations can be calculated and applied in a single step through the lasing process.

BRIEF DESCRIPTION OF THE DRAWINGS

These and other features and advantages of the present invention will be better understood by the following detailed description, taken together with the drawings wherein:

FIG. 2 is a schematic view of the human eye showing a measured ocular wavefront centered on the pupil;

FIG. 3 is a schematic view of the human eye showing a measured ocular wavefront shifted to center on the corneal intersect of the visual axis;

FIG. 4 is a schematic view of the human eye showing a reconstructed ocular wavefront centered on the corneal intersect of the visual axis.

DETAILED DESCRIPTION

Figure 1:
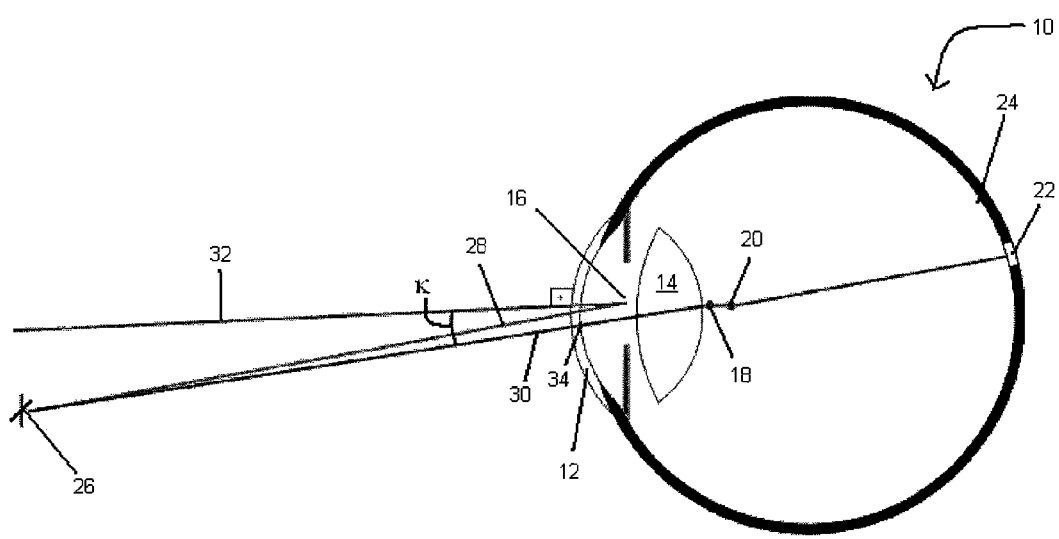
FIG. 1 is a schematic view of the human eye illustrating the important reference axes for refractive laser surgery.

Referring to FIG. 1, the visual perception of a human eye 10 depends on how rays of light are refracted by the cornea 12 and the lens 14. Ocular aberrations of the human eye 10 may be corrected by a typical refractive laser eye surgery, in which a patient is asked to focus on a fixation target 26 which is aligned with the optical axis of a laser, e.g., an excimer laser. The laser is programmed to perform an ablation pattern which is determined by a wavefront sensor or calculated from corneal topography. In most cases, this ablation pattern is centered on the pupil 16. Further, an eye tracking system is provided to ensure that the optical axis of the laser is always centered to the pupil 16. The axis defined by the center of the pupil 16 and the fixation target 26, when focused on by a patient, is the line of sight 28.

However, the physiological visual axis 30 of the human eye 10 is defined by the fixation target 26 and the real foveal image where the light passes through the nodal points 18 and 20. The fovea 22, a pit in the retina 24, is the point at which there is full acuity of vision. The location of nodal points 18 and 20 may be determined according to geometric construction principles. The difference between the line of sight 28 and the visual axis 30 will vary by patient. The location of the corneal intersect 34 of the visual axis 30 may be, e.g., approximately located by the corneal reflex. Additionally, the displacement of the visual axis 30 from the line of sight 28 may be shown, e.g., by polar displacement on a topographical map of the cornea created, e.g., by an imaging program such as OrbScan®. The degree of variance is represented by angle $\kappa$, measured between the visual axis 30 and the pupillary axis 32. The pupillary axis 32 is defined as a straight line passing through the center of the pupil 16 under normal incidence onto the cornea 12. In some cases, more accurate results would be obtained by an ablation pattern that is centered on the corneal intersect 34 of the visual axis 30 rather than the center of the pupil 16 since the latter does not represent aberrations from a patient's perspective. This is especially true for patients having a large angle $\kappa$ since the patient is looking out of the pupil 16 at the fixation target 26 along the visual axis 30, not along the line of sight 28.

In common practice, ocular aberrations are measured by a wavefront sensor, such as a Shack-Hartmann wavefront sensor. A typical Shack-Hartmann sensor comprises a light source, usually a laser or a diode, which sends a concentrated beam of light through an array of lenses and into the eye. Light is reflected back from a point on the retina 24 and out of the eye 10 through the pupil 16. The wavefront exiting the eye 10 falls upon the array of lenses and the degree of displacement from each lenslet center is detected. The locations of the spots depend on the local slope of the wavefront. An eye 10 without optical aberrations will have a flat wavefront, thereby projecting the spot through the center of a respective lenslet. The ocular wavefront is constructed from the spot displacements and quantified. Since the emerging wavefront is directly related to image quality within the eye, both lower-order aberrations, such as defocus and astigmatism, and higher-order aberrations, such as coma and spherical aberration, are detected. Wavefront data can also be generated from other suitable devices such as Anterior Chamber OCT, Scheimpflug camera, or the like.

The raw data taken from the wavefront sensor is an expression of local tilts which, when averaged over the area of each lenslet, approximates the ocular wavefront. The ocular wavefront is then quantified, e.g., using a series of Zernike polynomials that are defined over and orthogonal to the unit disk. Zernike polynomials may be used to describe aberrations of the cornea 12 and the lens 14. For example, a second order Zernike polynomial corresponds to refractive errors, such as defocus or astigmatism, while third and fourth order Zernike polynomials may represent higher-order aberrations, such as coma and spherical aberration, respectively. Each Zernike polynomial is assigned a coefficient to give the proper weighting to a respective polynomial in the wavefront. Ordinarily, the Zernike coefficients are determined by a least squares fit of the Zernike polynomials over the measured local tilts. Taken together, the Zernike polynomials and coefficients can be used describe the shape of any wavefront over the pupil.

Ocular wavefronts are measured and determined relative to the line of sight 28, and therefore centered on the pupil 16. The determination of Zernike polynomials and coefficients is correspondingly made with reference to the center of the pupil 16. Accordingly, the ablation pattern is centered along the line of sight 28. As discussed above, it may be preferable to center the ablation pattern on the corneal intersect 34 along the visual axis 30 rather than at the center of the pupil 16. However, using an ablation pattern based on the measured wavefront that is centered on the corneal intersect 34, a different point from which it was measured, results in wavefront decentration. For example, for a patient having a large angle $\kappa$, the measured aberrations will not correspond once the ablation pattern is moved to center on the corneal intersect 34. Thus, the measured wavefront must be recalculated using the visual axis 30 as the center.

Referring now to FIGS. 2-4, the progression of recentering the measured ocular wavefront 40 from the center of the pupil 16 to the corneal intersect 34 while maintaining the higher-order aberrations at the places they were measured is shown. FIG. 2 illustrates a measured ocular wavefront 40 taken using a wavefront sensor and centered over a large pupil 16. FIG. 3 illustrates a shift of the measured ocular wavefront 40 to center on the corneal intersect 34. As can be seen from a comparison of FIGS. 2 and 3, the measured ocular wavefront 40 of FIG. 3 does not coincide with the same corneal positions as measured in FIG. 2. Thus, a new coordinate center for the measured ocular wavefront 40 must be determined, e.g., by transforming the Zernike coefficients, as shown in FIG. 4. In order to correct higher-order aberrations while providing spherocylindrical correction, the reconstructed wavefront of FIG. 4 should replicate the measured wavefront of FIG. 2 and the pattern taken by the laser, e.g., ablation pattern, should center on the corneal intersect of the visual axis.

FIGS. 2-4 also illustrate the importance of reconstructing the measured ocular wavefront 40 and recentering on the corneal intersect 34. As can be seen in FIG. 2, a patient having a large angle κ perceives an aberration that is different than that aligned with the center of the pupil 16. FIG. 3 also does not show the aberrations from the patient's perspective, nor does the measured ocular wavefront 40 correspond to the required points on the cornea 12 for proper vision correction. FIG. 4, on the other hand, illustrates wavefront aberrations as perceived by the patient and centered on the visual axis 30. If the original measured ocular wavefront 40 is used to create an ablation pattern centered on the pupil 16 which attempts to correct a higher-order aberration, e.g., an apparent coma, it may cause an induced coma since the aberration it is attempting to fix is not necessarily the same aberration perceived by the patient, which could be, e.g., a positive spherical aberration; again, this is especially the case for patients having a large angle κ.

By providing a reconstructed wavefront, which may be derived either from a measured ocular wavefront, a corneal wavefront calculated in dependence on a corneal topography, or any combination thereof, having the visual axis 30 as its center, it is possible to provide a one-step procedure utilizing a customized ablation pattern that corrects both spherocylindrical and higher-order aberrations at the same time. In order to obtain the necessary decentered wavefront aberration data necessary to center the lasing process at the corneal intersect 34 of the visual axis 30, various solutions are provided below.

One possible solution would be to utilize a wavefront measuring device, i.e., an aberrometer, that is designed to determine the wavefront directly at the corneal intersect 34 of the visual axis 30, rather than along the line of sight 28. Another possible solution would be to transform or convert the aberration coefficients, e.g., the Zernike coefficients, to account for the decentration away from the measurement coordinates. Yet another solution would be to use primary and secondary raw data based on the line of sight wavefront measurements to reconstruct, reanalyze or reexpand the wavefront data for a different center coordinate. Primary raw data may be, e.g., the wavefront slope data taken by a Shack-Hartmann wavefront sensor, while secondary raw data refers to pre-processed data such as, e.g., reconstructed wavefront height data expanded through a set of Zernike aberrations. Once the reconstructed wavefront is determined for a new coordinate center it may be implemented into the aberrometer or any other system handling the wavefront data, such as, e.g., customized ablation software.

In accordance with one of the foregoing solutions, the aberration coefficients may be transformed using an available algorithm to provide a coordinate center shift of the wavefront and/or to expand it over a different sized pupil, or reference pupil. A wavefront is measured centered on the pupil as provided by, e.g., a Shack-Hartmann wavefront sensor. The obtained wavefront raw data is quantified in terms of either Zernike or Taylor polynomials or by a Fourier series or Seidel matrix to provide incoming coefficients based on the measurement pupil and line of sight centration. One way to transform the aberration coefficients would be to use a two-dimensional Taylor series expansion.

Alternatively, the incoming coefficients could be limited in number or order, e.g., to sixth-order Zernike polynomials, and the transformation for decentration of the wavefront could be provided preferably by the same number or order of outgoing coefficients. As an additional alternative, a generating, iterative derivation operator could be implemented within a computer program to transform, e.g., incoming Zernike coefficients regardless of their order, e.g., beyond sixth-order Zernike polynomials. According to any of the foregoing solutions, it is physically not meaningful for the Zernike coefficients to be part of a higher-order aberration state than that of the incoming measured Zernike order, thus preventing mixture into higher aberration states. Once the outgoing or transformed coefficients have been determined, they may be used to construct the new shifted wavefront for the calculation of the customized ablation pattern centered on the corneal intersect of the visual axis in a single step.

In accordance with another solution, the wavefront may be reconstructed with a new coordinate center through the manipulation of primary and secondary data taken by a wavefront sensor. As above, the Shack-Hartmann wavefront sensor may be used to provide raw data relating to the slope of the wavefront and incoming Zernike coefficients based upon a line of sight centration. The wavefront may then be reconstructed by expanding the incoming coefficients, if required, or by direct use of the primary and secondary raw data. The Zernike coefficients are transformed to fit the wavefront to a new coordinate center by, e.g., using a new coefficient base to describe the wavefront aberrations from the visual axis. This new coefficient base may be used to construct the new shifted wavefront for the calculation of the customized ablation pattern centered on the corneal intersect of the visual axis in a single step.

Figure 5:
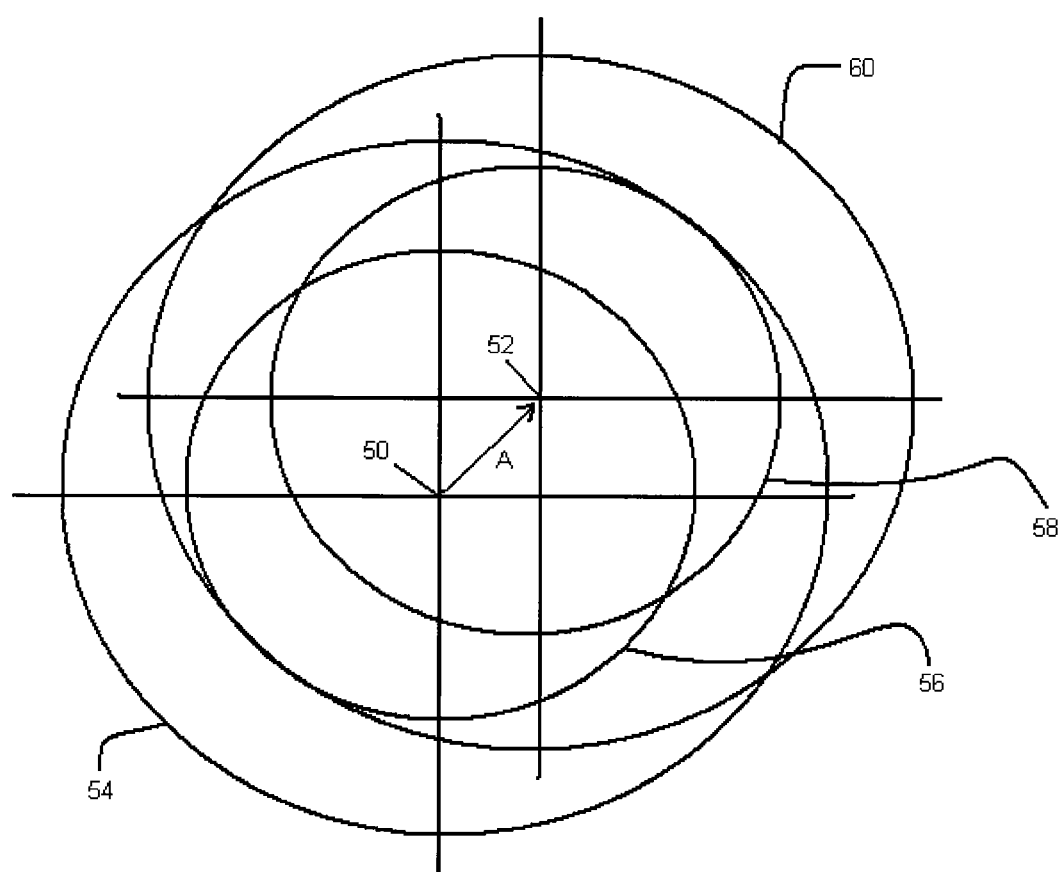
FIG. 5 is a schematic view of measurement and reference pupils illustrating the principle of wavefront data coordinate center shift in accordance with the present invention.

Referring now to FIG. 5, the principle of wavefront data coordinate shift is illustrated. The desired shift from the reference center 50, e.g., the center of the pupil, to the new coordinate center 52, e.g., the corneal intersect of the visual axis, is shown in direction A. The location of corneal intersect of the visual axis could be measured, determined by geometric construction principles, or is preferably best approximated by the corneal reflex. The reference shift is indicated by direction A and measured between the reference center 50 and the new coordinate center 52.

Where Zernike polynomials are defined over a measured reference pupil 56, it is possible to expand the Zernike coefficients to define over a shifted reference pupil 58. However, in such a case, it may be required to extrapolate data in areas where no original measurement raw data exists, i.e., the area within the shifted reference pupil 58, but outside the measured reference pupil 56. If, on the other hand, wavefront data is taken on an original measurement pupil 54, which is possible due to dilation, the need to extrapolate may be avoided. The wavefront taken on the original measurement pupil 54 may be reduced to cover only the measured reference pupil 56. As long as the diameter of the measured reference pupil 56 is less than or equal to the diameter of the original measurement pupil 54 minus the length of the reference shift, the new wavefront over the shifted reference pupil 58 will always be reconstructed or expanded on the basis of real and available original wavefront data taken from the original measurement pupil 54, i.e., fully-backed up by measurement data.

In a case where the diameter of the measured reference pupil 56 is greater than the diameter of the original measurement pupil 54 minus the length of the reference shift, reconstruction or expansion of the new wavefront will extend partly into an area where no real wavefront data is available. In such a case, the original measured wavefront could be extrapolated, e.g., by expansion of the incoming Zernike coefficients onto an extended diameter or, alternatively, the points for which no measurement data is available could be left out of the Zernike reconstruction. Thus, when using the transformed coefficients to create the new wavefront for an ablation pattern centered on the new coordinate center 52, the wavefront will be uncertain to a certain extent in the area where no real measurement data is available. However, there is generally a small degree of uncertainty with nearly all measurements, such as, e.g., the area between sampling points of a Shack-Hartmann wavefront sensor. Further, any limitation in reconstruction order, e.g., to sixth-order Zernike polynomials, introduces uncertainties, especially regarding the periphery of the fit. Nevertheless, as long as extrapolation is limited to reasonable diameters, an accurate ablation pattern can still be achieved. For example, it is expected that measured wavefront data may be extendable in diameter by about 10% for a typical human eye having a fairly regular cornea.

In another embodiment, however, the solution provides a shifted wavefront over a new coordinate center 52 which also exactly reproduces the wavefront as originally measured over the measured reference pupil 56 without any extrapolated data entering into the ablation pattern calculation. A new analysis pupil 60 centered on the new coordinate center 52 and having a diameter at least large enough to tangentially encompass the measured reference pupil 56 is determined. As shown in FIG. 5, this new analysis pupil 60 includes both the measured reference pupil 56 and the shifted reference pupil 58. In this embodiment, Zernike polynomials will not be orthogonal over the partially filled areas and these non-orthogonal polynomials should be treated like any other non-orthogonal polynomials, such as, e.g., Taylor polynomials having powers in the Cartesian $x''y'''$ format. The measured or incoming Zernike polynomials, or the original measured wavefront data, are used to provide the surface data over the measured reference pupil 56 and the surface data over the new analysis pupil 60 is determined by performing a least squares wavefront reconstruction fit using data from the original measured wavefront only. The resulting surface data over the new analysis pupil 60 provides a new set of Zernike coefficients can be used to directly perform an ablation pattern centered on the new coordinate center 52 within the area encompassed by the original measurement pupil. This may be done, e.g., by using customized ablation software implementing ablation algorithms. Accordingly, manifest refractions or corrections can be made at the new coordinate center 52 without changing the higher-order corrections as determined by the original wavefront measurement.

Preferably, all data outside the measured reference pupil 54 is masked since the actual location of the patient's pupil has not changed, only the mathematical representation of it has. While data outside the area of the original pupil is an extrapolation which is ignored in one embodiment, it may be useful as a good analytic continuation of data outside the area of the original pupil, thereby leading to better transition zones.

A Shack-Hartmann wavefront sensor is the preferable, and most widely-used, wavefront sensor. However, it is noted that any suitable wavefront sensor may be used in the inventive method described herein. Similarly, while Zernike polynomials are preferable to quantify the data from the wavefront sensor, it is noted that the aberration coefficients may be any combination of Zernike, Seidel, Taylor, Fourier or like representations. Likewise, wavefronts may be given as ocular wavefronts (either ocular or corneal), in the form of height data, as respective slope data (i.e., derivations of the height data) or as aberration coefficients based on different series of orthogonal polynomial data sets. Further, the new coordinate center 52 is preferably the corneal intersect 34 of the visual axis 30, but it is noted that the above methods may be applied to provide a modified wavefront centered over any point on the cornea, such as at the first Purkinje Reflex, i.e., the corneal light reflex. Alternatively, it may center near the corneal intersect of the visual axis, near the Purkinje Reflex or at any point therebetween.

While the invention has been particularly shown and described with reference to preferred embodiments thereof, it will be understood by those skilled in the art that various changes in form and details may be made therein without departing from the spirit and scope of the invention.

We claim:

1. A method of creating a pattern to be followed by a laser over a new coordinate center comprising the steps of:
   measuring an original wavefront centered on a center of a pupil;
   quantifying the original wavefront in terms of aberration polynomials, each aberration polynomial being weighted by an aberration coefficient;
   determining a shift from the center of the pupil to the new coordinate center, the new coordinate center being located at an approximation of or on the visual axis of the eye at an intersection of a cornea of the eye;
   transforming the aberration coefficients based on the shift, wherein the transformed aberration coefficients define a reconstructed wavefront; and
   creating the pattern for the laser from the reconstructed wavefront, wherein the pattern is centered over the new coordinate center.

2. The method of claim 1, wherein the pattern is an ablation pattern and the laser is an excimer laser.

3. The method of claim 1, wherein the pattern is a lenticule generation pattern and the laser is a femtosecond laser.

4. The method of claim 1, further comprising the step of expanding the aberration coefficients over a diameter larger than the pupil after the quantifying step.

5. The method of claim 1, wherein the aberration polynomials are Zernike polynomials and the aberration coefficients are Zernike coefficients.

6. The method of claim 1, wherein the measuring step is performed using an aberrometer.

7. The method of claim 6, wherein the aberrometer is a Shack-Hartmann wavefront sensor.

8. A method of performing refractive laser eye surgery on a human eye comprising the steps of:
   measuring an original wave front centered on a center of a measurement pupil;
   determining an analysis pupil encompassing the measurement pupil, wherein the analysis pupil is centered on a new coordinate center at an approximation of or on the visual axis of the eye at an intersection with a cornea of the eye;
   generating surface data from the original wavefront for the areas covered by the measurement pupil;
   performing a least squares wavefront reconstruction fit over the analysis pupil using the surface data so as to provide a reconstructed wavefront; and
   creating a pattern to be followed by a laser from the reconstructed wavefront, wherein the pattern is centered on the new coordinate center.

9. The method of claim 8, wherein the pattern masks the surface data falling outside of the measurement pupil.

10. The method of claim 8, wherein the original wavefront is quantified in terms of aberration polynomials, each aberration polynomial weighted by an aberration coefficient.

11. The method of claim 10, wherein the reconstructed wavefront is quantified by a transformation of the aberration coefficients.

12. The method of claim 11, wherein the aberration coefficients are Zernike coefficients.

13. The method of claim 12, wherein the aberration coefficients and the transformed aberration coefficients are of the same order.

14. The method of claim 8, wherein the new coordinate center is located at the intersection of a cornea and a visual axis of the human eye.

15. The method of claim 8, wherein the surface data comprises a series of slopes generated in the measuring step.

16. The method of claim 8, wherein the pattern is an ablation pattern and the laser is an excimer laser.

17. The method of claim 8, wherein the pattern is a lenticule generation pattern and the laser is a femtosecond laser.

18. The method of claim 8, further comprising the step of: adjusting the shape of a cornea using the laser, wherein the laser follows the pattern.

19. A method of generating a laser pattern centered on a new coordinate center comprising the steps of:
generating primary and secondary raw data from an aberrometer operating over a pupil along a line of sight, wherein the line of sight is defined between the center of a fixation target and a center of the pupil;
generating a reconstructed wavefront from the primary and secondary raw data based on a shift from the line of sight to the new coordinate center, the new coordinate center being located at an approximation of or on the visual axis of the eye at an intersection with a cornea of the eye; and
creating the laser pattern using the reconstructed wavefront, wherein the laser pattern is centered on the new coordinate center.

\* \* \* \* \*